US009759773B2

(12) United States Patent
Ledbetter

(10) Patent No.: US 9,759,773 B2
(45) Date of Patent: *Sep. 12, 2017

(54) SYSTEM AND METHOD TO PREDICT A USABLE LIFE OF A VACUUM INTERRUPTER IN THE FIELD

(71) Applicant: Finley Lee Ledbetter, Argyle, TX (US)

(72) Inventor: Finley Lee Ledbetter, Argyle, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/740,245

(22) Filed: Jun. 15, 2015

(65) Prior Publication Data

US 2015/0285863 A1 Oct. 8, 2015

Related U.S. Application Data

(63) Continuation-in-part of application No. 14/694,737, filed on Apr. 23, 2015, which is a continuation of application No. 13/455,608, filed on Apr. 25, 2012, now Pat. No. 9,026,375.

(60) Provisional application No. 61/570,247, filed on Dec. 13, 2011, provisional application No. 61/570,253, filed on Dec. 13, 2011, provisional application No. 61/570,258, filed on Dec. 13, 2011.

(51) Int. Cl.
*G01R 31/327* (2006.01)
*H01H 33/668* (2006.01)

(52) U.S. Cl.
CPC ....... *G01R 31/3274* (2013.01); *G01R 31/327* (2013.01); *G01R 31/3275* (2013.01); *H01H 33/668* (2013.01)

(58) Field of Classification Search
None
See application file for complete search history.

(56) References Cited

U.S. PATENT DOCUMENTS

| | | | |
|---|---|---|---|
| 3,378,761 A | 4/1968 | Morgan | |
| 4,163,130 A | 7/1979 | Kubota et al. | |
| 4,440,995 A | 4/1984 | Lange et al. | |

(Continued)

FOREIGN PATENT DOCUMENTS

| | | |
|---|---|---|
| EP | 0079181 B1 | 3/1986 |
| GB | 1067769 A | 5/1967 |

(Continued)

OTHER PUBLICATIONS

Predicting the Remaining Life of Vacuum Interrupters in the Field; NETA World Journal; 2012; pp. 1-5.

(Continued)

*Primary Examiner* — Jermele M Hollington
*Assistant Examiner* — Suresh K Rajaputra
(74) *Attorney, Agent, or Firm* — Gardere Wynne Sewell LLP

(57) ABSTRACT

A closed and open contact method to predict a usable life of vacuum interrupters in the field can include using computer instructions in the data storage to instruct the processor to position a calculated amp or calculated pressure on an ionic or current versus pressure calibration curve for the installed vacuum interrupter and identify trend data from a library of trend data corresponding to the installed vacuum interrupter and to the calculated pressure or calculated amp of the installed vacuum interrupter; thereby determining the anticipated life expectancy.

24 Claims, 12 Drawing Sheets

(56) References Cited

U.S. PATENT DOCUMENTS

| | | | |
|---|---|---|---|
| 4,484,818 A | 11/1984 | Houston | |
| 5,453,587 A | 9/1995 | Hurley et al. | |
| 5,710,536 A | 1/1998 | Fastman | |
| 8,824,116 B2 | 9/2014 | Smith et al. | |
| 9,026,375 B1 * | 5/2015 | Ledbetter | H01F 27/28 335/18 |
| 9,031,795 B1 | 5/2015 | Ledbetter | |
| 9,335,378 B2 * | 5/2016 | Ledbetter | H01F 27/28 |
| 2008/0309437 A1 * | 12/2008 | Smith | H01H 1/0015 335/18 |
| 2012/0063631 A1 | 3/2012 | Choi et al. | |
| 2015/0226803 A1 * | 8/2015 | Ledbetter | H01F 27/28 702/34 |
| 2015/0226804 A1 | 8/2015 | Ledbetter | |

FOREIGN PATENT DOCUMENTS

| | | |
|---|---|---|
| JP | 04132131 A | 5/1992 |
| JP | 08180776 A | 7/1996 |
| JP | 2003219500 A | 7/2003 |
| JP | 2006165774 A | 6/2006 |
| JP | 2010197132 A | 9/2010 |
| JP | 2012070164 A | 4/2012 |
| WO | WO-2010131794 A1 | 11/2010 |

OTHER PUBLICATIONS

Zha Ziyu, Jiang Ziuchen, and Jin Zhijian; Study on Internal Pressue Measurement of Vacuum Interrupter; IEEE 19th International Symposium on Discharges and Electrical Insulation in Vacuum; 2000; pp. 775-778.
International Search Report dated Mar. 8, 2013 in PCT/US2012/069211.
Written Opinion mailed Mar. 8, 2013 in PCT/US2012/069211.
International Preliminary Report on Patentability for Co-Pending PCT Application No. PCT/US2012/069211 dated Jun. 17, 2014, 6 pgs.
International Search Report and Written Opinion in corresponding international application PCT/US2016/037699, dated Oct. 21, 2016, 11 pages.
Australian First Examination Report for Co-Pending Australian Application No. 2012352393 dated May 15, 2015, 3 pgs.
UK Search Report for Co-Pending UK Application No. 1410831.0, dated Dec. 16, 2015, 2 pgs.
JP-08180776-A, Hitachi Ltd., publication date: Jul. 12, 1996, English translation.

* cited by examiner

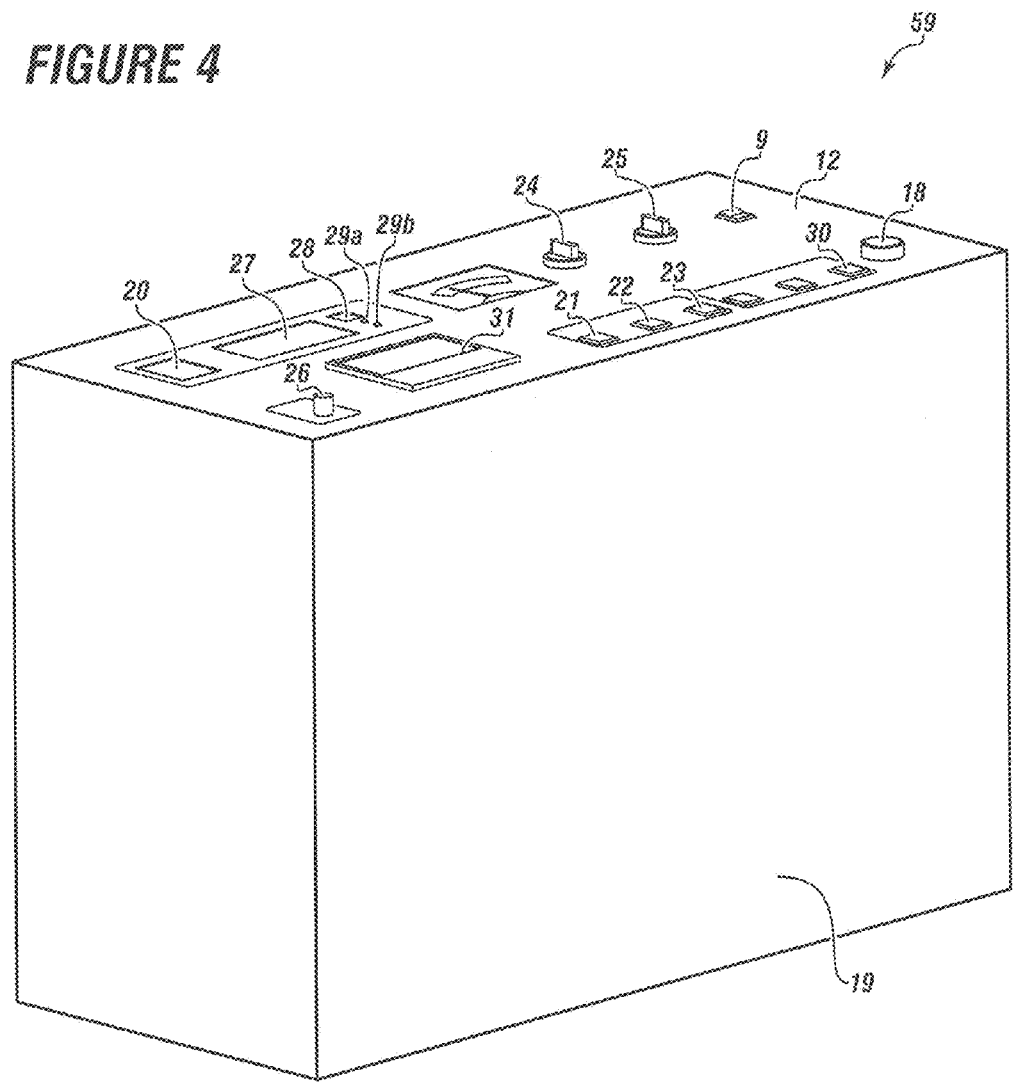

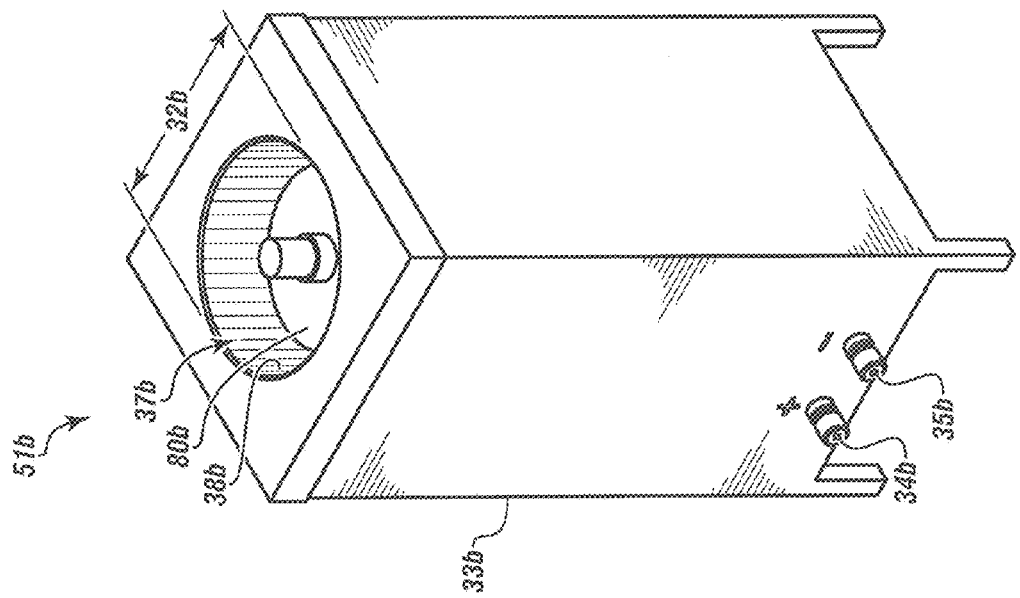
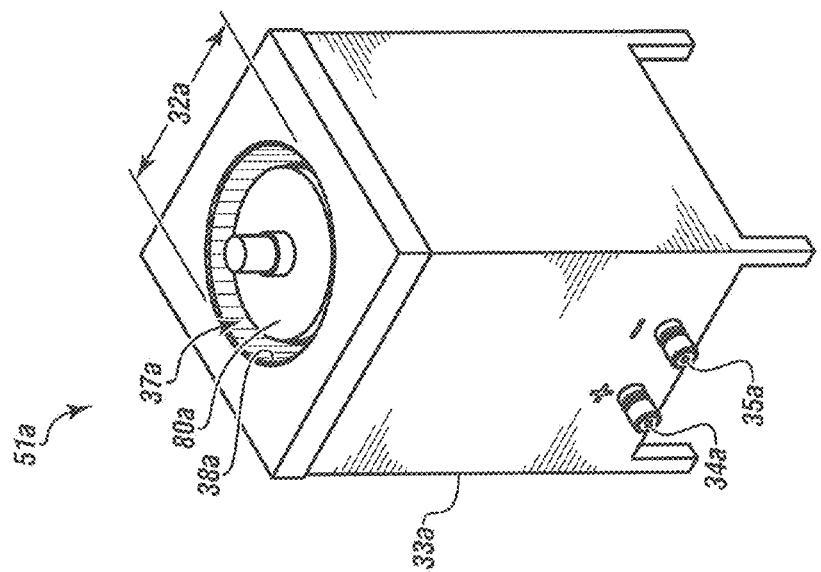

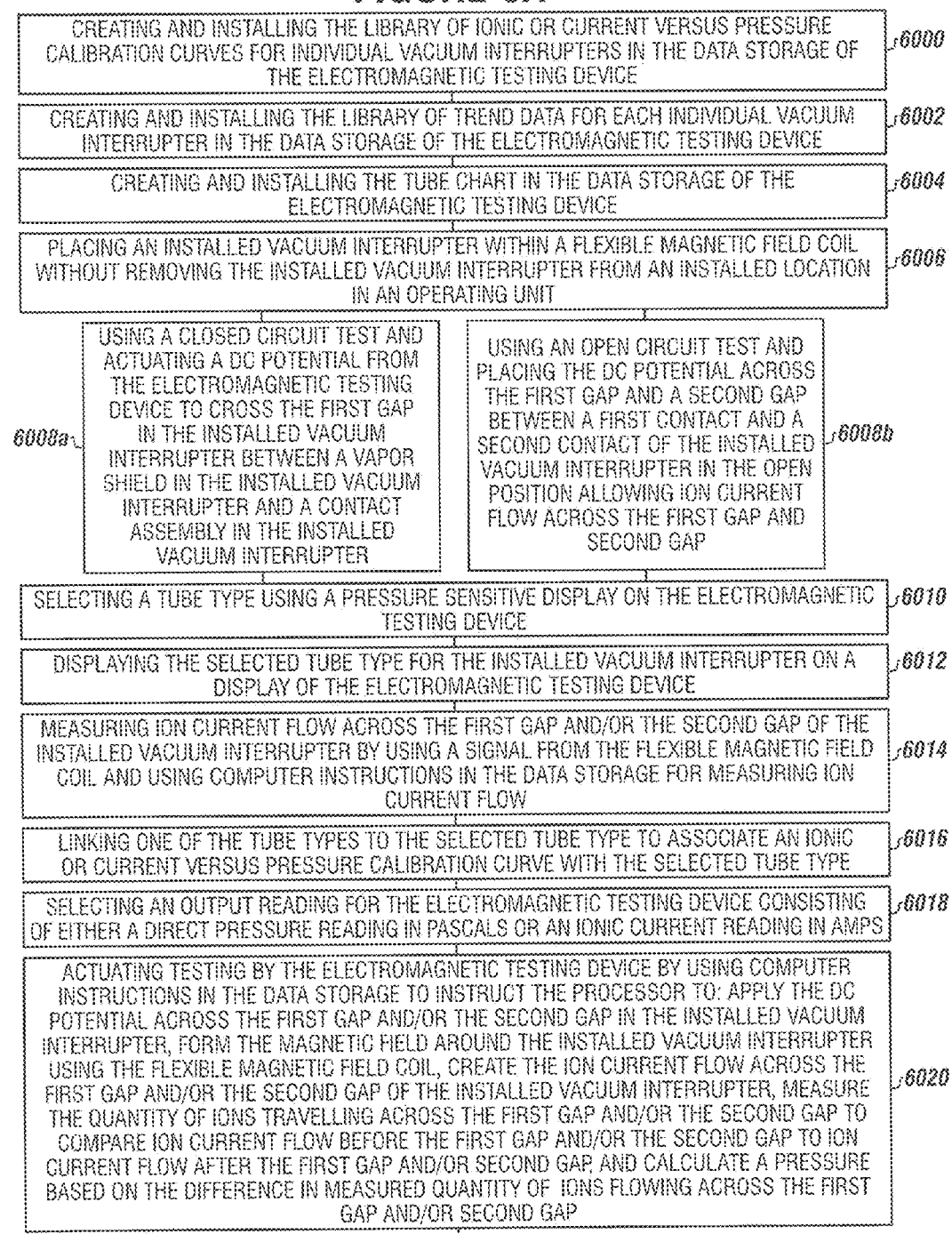

(6A)

| | |
|---|---|
| USING A CLOSED CIRCUIT TEST AND ACTUATING A DC POTENTIAL FROM THE ELECTROMAGNETIC TESTING DEVICE TO CROSS THE THIRD GAP IN THE INSTALLED VACUUM INTERRUPTER BETWEEN THE VAPOR SHIELD IN THE INSTALLED VACUUM INTERRUPTER AND THE CONTACT ASSEMBLY IN THE INSTALLED VACUUM INTERRUPTER | 6022 |
| MEASURING ION CURRENT FLOW ACROSS THE THIRD GAP OF THE INSTALLED VACUUM INTERRUPTER BY USING A SIGNAL FROM THE FLEXIBLE MAGNETIC FIELD COIL AND USING COMPUTER INSTRUCTIONS IN THE DATA STORAGE FOR MEASURING ION CURRENT FLOW | 6024 |
| ACTUATING TESTING BY THE ELECTROMAGNETIC TESTING DEVICE BY USING COMPUTER INSTRUCTIONS IN THE DATA STORAGE TO INSTRUCT THE PROCESSOR TO: APPLY THE DC POTENTIAL ACROSS THE THIRD GAP IN THE INSTALLED VACUUM INTERRUPTER, FORM THE MAGNETIC FIELD AROUND THE INSTALLED VACUUM INTERRUPTER USING THE FLEXIBLE MAGNETIC FIELD COIL, CREATE THE ION CURRENT FLOW ACROSS THE FIRST GAP AND/OR THE SECOND GAP OF THE INSTALLED VACUUM INTERRUPTER, MEASURE THE QUANTITY OF IONS TRAVELLING ACROSS THE THIRD GAP TO COMPARE ION CURRENT FLOW BEFORE THE THIRD GAP TO ION CURRENT FLOW AFTER THE THIRD GAP, AND CALCULATE A PRESSURE BASED ON THE DIFFERENCE IN MEASURED QUANTITY OF IONS FLOWING ACROSS THE THIRD GAP | 6026 |
| DETERMINING AN ANTICIPATED LIFE EXPECTANCY OF THE INSTALLED VACUUM INTERRUPTER BY: POSITIONING THE CALCULATED AMP OR CALCULATED PRESSURE ON THE IONIC OR CURRENT VERSUS PRESSURE CALIBRATION CURVE FOR THE INSTALLED VACUUM INTERRUPTER AND IDENTIFYING THE TREND DATA FROM THE LIBRARY OF TREND DATA CORRESPONDING TO THE INSTALLED VACUUM INTERRUPTER AND TO THE CALCULATED PRESSURE OR TO THE CALCULATED AMP OF THE INSTALLED VACUUM INTERRUPTER TO DETERMINE THE ANTICIPATED LIFE EXPECTANCY IN YEARS AND MONTHS FOR THE INSTALLED VACUUM INTERRUPTER | 6028 |
| PROVIDING THE CALCULATED AMP OR CALCULATED PRESSURE TO AN RS232 INTERFACE OR A PRINTER | 6030 |
| USING A PRINTER THAT IS INTEGRATED WITH THE ELECTROMAGNETIC TESTING DEVICE TO PRINT THE CALCULATED AMP OR CALCULATED PRESSURE AND TO PROVIDE A LOCATION OF THE CALCULATED AMP OR CALCULATED PRESSURE ON THE IONIC OR CURRENT VERSUS PRESSURE CALIBRATION CURVE OF THE INSTALLED VACUUM INTERRUPTER | 6032 |
| RESETTING THE DISPLAY USING A RESET BUTTON ON THE ELECTROMAGNETIC TESTING DEVICE TO: TURN OFF AN LED LIGHT, CLEAR THE CALCULATED AMP, CLEAR THE CALCULATED PRESSURE, OR COMBINATIONS THEREOF | 6034 |
| USING THE LED LIGHT TO INDICATE WHEN THE ELECTROMAGNETIC TESTING DEVICE IS PERFORMING THE TEST | 6036 |
| CONNECTING THE PROCESSOR WITH A NETWORK FOR COMMUNICATION TO A CLIENT DEVICE REMOTE TO THE PROCESSOR | 6038 |

*FIGURE 6B*

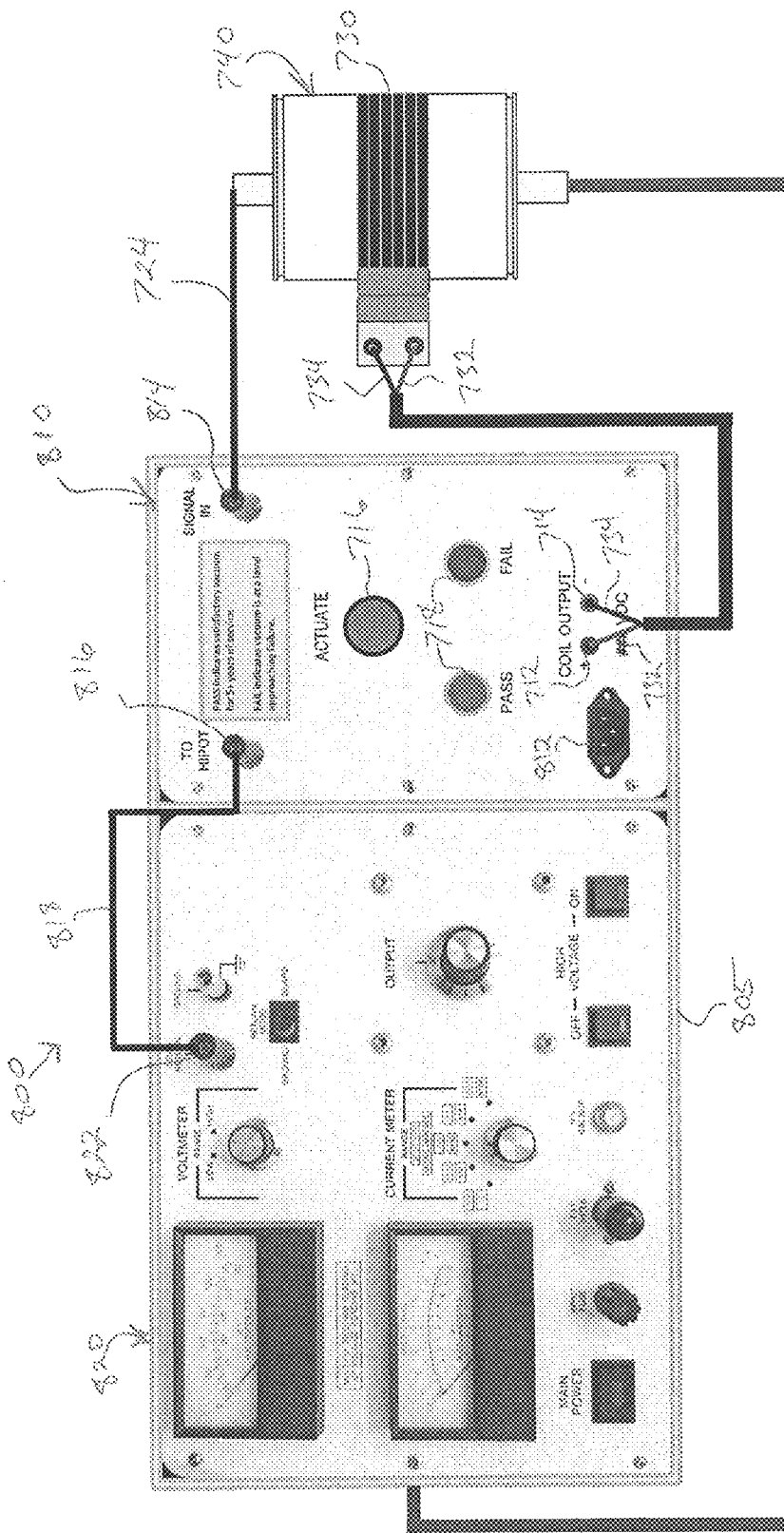

SYSTEM AND METHOD TO PREDICT A USABLE LIFE OF A VACUUM INTERRUPTER IN THE FIELD

CROSS REFERENCE TO RELATED APPLICATIONS

Pursuant to 35 U.S.C. §120, this application is a continuation-in-part of, and incorporates by reference for all purposes, U.S. patent application Ser. No. 14/694,737, entitled "METHOD TO PREDICT A USABLE LIFE OF A VACUUM INTERRUPTER IN THE FIELD," filed Apr. 23, 2015, which is a continuation of U.S. patent application Ser. No. 13/455,608, entitled "METHOD TO PREDICT A USABLE LIFE OF A VACUUM INTERRUPTER IN THE FIELD," filed Apr. 25, 2012, which claims the benefit of U.S. Provisional Application No. 61/570,247, entitled "METHOD TO PREDICT A USABLE LIFE OF A VACUUM INTERRUPTER IN THE FIELD," filed Dec. 13, 2011, U.S. Provisional Application No. 61/570,253, entitled "ELECTROMAGNETIC TEST DEVICE TO PREDICT A USABLE LIFE OF A VACUUM INTERRUPTER IN THE FIELD," filed Dec. 13, 2011, and U.S. Provisional Application No. 61/570,258, entitled "FLEXIBLE MAGNETIC FIELD COIL FOR MEASURING IONIC QUANTITY," filed Dec. 13, 2011, all of which naming Finley Lee Ledbetter as inventor, and all of which is incorporated by reference for all purposes.

FIELD

The present embodiments generally relate to a method to predict a useful life expectancy of vacuum interrupters while the vacuum interrupters are installed in the field.

BACKGROUND

A need exists for a fast and reliable method to test vacuum interrupters of circuit breakers to determine the usable life expectancy thereof without having to remove the vacuum interrupters from their installed positions in the field.

A need exits for a method to determine the usable life expectancy of vacuum interrupters in the field that can reduce the occurrence of electrical failures, death, and destruction in the field.

A need exists for a method to test vacuum interrupters that can avoid the introduction of X-rays into work environments; thereby providing safe and healthy work environments.

The present embodiments meet these needs.

BRIEF DESCRIPTION OF THE DRAWINGS

The detailed description will be better understood in conjunction with the accompanying drawings as follows:

FIG. 4 depicts the electromagnetic testing device according to one or more embodiments.

FIGS. 5A and 5B depict detailed views of two different types of fixed inner diameter magnetic coils.

FIGS. 6A and 6B depict a diagram of the method according to one or more embodiments.

FIGS. 8A and 8B illustrate an example of a partially integrated embodiment of the electromagnetic testing device.

Figure 1:
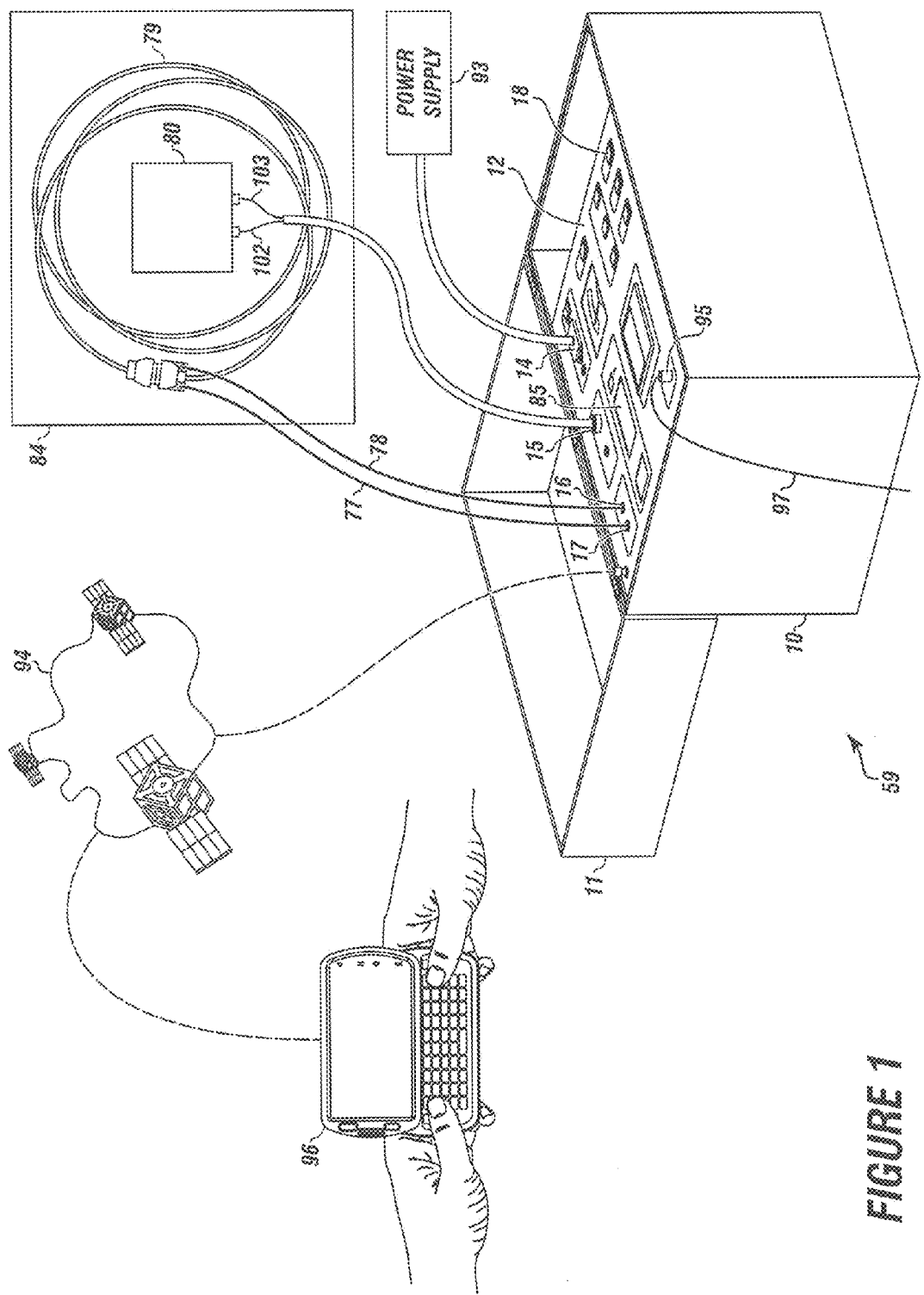
FIG. 1 depicts an electromagnetic testing device connected to a flexible magnetic field coil, power supply, and an installed vacuum interrupter using a positive engagement wire and a negative engagement wire according to one or more embodiments.

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

Historically, air magnetic and oil interrupters were the only types of interrupters used on circuit breakers rated at 2.4 kilovolts (kV) or higher, with air magnetic interrupters being used on lower voltages in this rating, including voltages ranging from 2.4 kV to 25 kV, and with oil interrupters being most commonly used on voltages higher than 25 kV, primarily because of their ability to interrupt higher arc energies.

Air magnetic interrupters degrade somewhat each time they are opened under load, and degrade significantly when they are interrupted under fault. Contacts can be repaired or replaced if required; however, maintenance of such circuit breakers is not always properly scheduled, which can result in failures.

In addition to maintenance issues, arc-chutes are large and heavy, and some are chutes are fragile and can be broken if not properly handled.

Oil interrupters are heavy and submerged in oil, such that reaching the oil interrupters for inspection is difficult. As such, oil interrupters are not always maintained as they should be.

The present embodiments relate to a method for vacuum interrupters that provides for ease of testing and maintenance of the vacuum interrupters, use of flexible and lightweight testing equipment, and allowance for testing in the field, each of which is not available with prior testing methods for vacuum interrupters in the field.

One or more of the present embodiments relate to a closed contact method to predict a usable life of installed vacuum interrupters in the field, as well as to an open contact method to predict the usable life of installed vacuum interrupters in the field.

The method can include using fixed size portable magnetic coils, which can be lightweight and easy to use.

In embodiments, the method can be used on vacuum interrupters that are compact and sealed.

The method can be used on vacuum interrupters that have short gap travel distances, such as gap travel distances ranging from about 8 mm to about 12 mm.

The method can cause less damage than other methods for testing vacuum interrupters.

The method involves creating a plurality of ionic or current versus pressure curves as models of the useful life of different sized vacuum interrupters, as well as storing the plurality of ionic or current versus pressure curves in a library in the data storage.

The method further involves creating a plurality of trend data for expected life of different vacuum interrupters using pressure and other variables, as well as storing the trend data in a trend data library in the data storage.

The method has as a step creating a tube chart, which can include different values with different points. In operation, an individual vacuum interrupter can be tested to meet criteria that are different than criteria met by other individual vacuum interrupters. As such, a unique point value can be created for each criteria of each individual vacuum interrupter. The sum of the points can be placed into a unique algorithm that can utilize the trend data in the data storage to determine life expectancy for individual vacuum interrupters.

For example, a first point value can be assigned based on a model number and the type of vacuum interrupter being tested. For example, a GE 40A1, 12 KV, 1200 amp, 18 KA vacuum interrupter can have a high first point value for reliability.

The second point value can be a point value that depends on how many operations the individual vacuum interrupter has been used in. For example, 1-100 operations on the GE 40A1 can have a second point value of 5 points assigned to it, 101 to 1000 operations on the GE 40A1 can have a second point value of 6 points assigned to it, 1001 to 2000 operations on the GE 40A1 can have a second point value of 7 points assigned to it, 2001 to 3000 operations on the GE 40A1 can have a second point value of 8 points assigned to it, and over 3001 operations on the GE 40A1 can have a second point value of 9 points assigned to it. The second point value can vary depending upon the particular individual vacuum interrupter and the number of operations it has been used in.

A third point value can relate to an age of the individual vacuum interrupter. For example, a 5 year old vacuum interrupter can have 5 points assigned to it as the third point value, a 10 year old vacuum interrupter can have 6 points assigned to it as the third point value, a 15 year old vacuum interrupter can have 7 points assigned to it as the third point value, a 20 year old vacuum interrupter can have 8 points assigned to it as the third point value, and a 25 year old vacuum interrupter can have 9 points assigned to it as the third point value. The third point value can vary depending upon the particular individual vacuum interrupter and the age of the particular individual vacuum interrupter.

A fourth point value can be for contact resistance and wear information for the individual vacuum interrupter. For example, if 30 micro Ohms are measured, which means 80 percent of a contact surface remains for a particular individual vacuum interrupter, then the fourth point value can be 5, if 40 micro Ohms are measured, which means 60 percent of the contact surface remains, then the fourth point value can be 6, if 50 micro Ohms are measured, which means 40 percent of the contact surface remains, then the fourth point value can be 7, if 60 micro Ohms are measured, which means 20 percent of the contact surface remains, then the fourth point value can be 8, and if 70 micro Ohms are measured, which means 10 percent of the contact surface remains, then the fourth point value can be 9. The fourth point value can vary depending upon the particular individual vacuum interrupter and the amount of Ohms measured for the particular individual vacuum interrupter.

A fifth point value that can be used for the calculation of life expectancy of the vacuum interrupters can be based on results obtained using the electromagnetic testing device with specific vacuum interrupters.

In operation, the method has the vacuum interrupter rating 5 points when tested at a pressure of 10×E-6, rating 4 points when tested at a pressure of 10×E-5, rating 3 points when tested at a pressure of 10×E-4, rating 8 points when tested at a pressure of 5.0×E×10-3, and rating 9 points when tested at a pressure of 10×E-3.

The calculation of the life expectancy can factor in a weighting value based on the number of vacuum interrupters tested with similar results. For example, for 1-100 samples of a certain vacuum interrupter, the weighting value can be 1.5, for 101-200 samples the weighting value can be 1.4, for 201-300 samples the weighting value can be 1.3, for 301-400 samples the weighting value can be 1.2, for 401-500 samples the weighting value can be 1.1, and for vacuum interrupters that have had samples tests more than 500 times the weighting value can be 1.0.

A primary basis for the wide acceptance of vacuum interrupters is financial. A life span and the number of vacuum interrupters can be increased using the method disclosed herein. The method can allow the life span for vacuum interrupters to range from about five times to about ten times longer, particularly for SF-6 vacuum interrupters.

The method can use simple yet ruggedly constructed equipment to test the vacuum interrupters.

In operation, all of the point values can be added together to attain a total value for the vacuum interrupter. For example, all of the point values can be added together to equal 20 for a particular vacuum interrupter with a long life expectancy. A larger total value would indicate a need to replace the vacuum interrupter sooner than vacuum interrupters having a lower total value.

The total value of point values can be multiplied by the weighting value based on a sample size to provide a point value, and the life expectancy can be determined based on a category that the point value falls into.

If the point value is between 20 and 30, this can indicate a long life expectancy and that the vacuum interrupter needs to be checked in 10 years.

If the point value is between 30 and 34, this can indicate that the vacuum interrupter will need to be checked and probably replaced in 5 years.

If the point value is between 35 and 44, this can indicate that the vacuum interrupter will need to be checked in 2 years and probably replaced in 2 years.

If the point value is over 45, this can indicate that the vacuum interrupter is about to fail and should be replaced immediately.

The use of the weighting value can yield a better and more accurate result. Computer instructions can be formed and/or stored in the data storage to perform calculation of the life expectancy for each vacuum interrupter.

The method can include using an electromagnetic testing device connected to a flexible magnetic field coil to perform testing.

The method can also utilize calibration information, which can be created without the electromagnetic testing device, and can be installed for use on the electromagnetic testing device.

The calibration information can include an ionic or current versus pressure calibration curve for each model vacuum interrupter.

The calibration information can be formed by testing a specific individual model of a vacuum interrupter, which can have a vacuum created therein for testing at 40 different ionic currents to determine 40 different points of calculated pressure or 40 different points of measured amps; thereby creating an ionic or current versus pressure calibration curve for a specific model of vacuum interruption.

Each ionic or current versus pressure calibration curve can be input into a library of ionic or current versus pressure calibration curves in the data storage connected to the processor; thereby allowing a user to select a vacuum interrupter model and obtain the corresponding ionic or current versus pressure calibration curve.

Additionally, a library of trend data can be created for each of the vacuum interrupters in the library of ionic or current versus pressure calibration curves. The trend data can be installed in the library of trend data in data storage associated with the processor.

The trend data can include: a vacuum pressure at a date of testing versus vacuum pressure when the vacuum interrupter was manufactured to provide a leak rate; circuit breaker type; circuit breaker serial number; date of vacuum interrupter manufacture; circuit breaker condition at ambient atmosphere; circuit breaker insulation resistance; circuit breaker operating condition, such as an alkaline condition or an acidic condition; serial number of the installed vacuum interrupter; vacuum interrupter wear indication data; installed vacuum interrupter contact resistance; circuit criticality, such as a level of importance of the circuit in the facility; manufacturer name for the installed vacuum interrupters; manufacturer part number; an approximate number of operations on the vacuum interrupter; circuit breaker atmosphere; or combinations thereof.

The method can include using the electromagnetic testing device with the data storage and the processor to perform testing.

The data storage with the associated processor can be a circuit board. The library of ionic or current versus pressure calibration curves and the library of trend data can be stored in the data storage.

Additionally, a tube chart can be installed in the data storage of the electromagnetic testing device.

The tube chart can be formed from a plurality of tube types. Each tube type can have a tube identifier, such as a model number or serial number. Each tube identifier can have a tube specific ionic or current versus pressure calibration curve.

A flexible magnetic field coil can be connected to the electromagnetic testing device. The flexible magnetic field coil can be a loop made from a plurality of insulated copper wires.

A positive pole and a negative pole can each be connected to the flexible magnetic field coil and connected to the electromagnetic testing device; thereby allowing the electromagnetic testing device to flow a high voltage to the flexible magnetic field coil when a test procedure is actuated.

The electromagnetic testing device can be connected to a power supply to allow the electromagnetic testing device to power the flexible magnetic field coil and to perform monitoring and calculation steps required for the testing.

The electromagnetic testing device can also be connected using a positive engagement wire to the installed vacuum interrupter at a tube end, and a ground engagement wire on another end. The electromagnetic testing device can then be connected to a ground.

The method can be used for testing vacuum interrupters in the field that have three gaps. The method can allow for testing of the gaps between internal contacts of the vacuum interrupter and a metal vapor shield of the vacuum interrupter.

The three gaps in the vacuum interrupters can include a first gap between a moving contact portion of a contact assembly and a fixed contact portion of the contact assembly, a second gap between the moving contact portion and the metal vapor shield of the vacuum interrupter, and a third gap between the fixed contact portion and the metal vapor shield.

The method can allow for simultaneous testing of all three gaps for leak detection. The method can prevent explosions of the vacuum interrupters by enabling quick and cheap field detection of leaks using flexible lightweight testing equipment.

The method can be used on vacuum interrupters that have metal vapor shields, which capture metal vapor or other contaminant particles created by metallic arcing that occurs when contacts open. The metal vapor shield can capture or inhibit the metal vapor or contaminant particles from entering the gap between the moving contact portion and the fixed contact portion.

The metal vapor or contaminant particles can be highly ionized, can cause thermal expansion, and can be drawn to the metal vapor shield by electrostatic forces. When the metal vapor or contaminant particles contact the metal vapor shield, the metal vapor or contaminant particles can quickly solidify and adhere to the metal vapor shield, which can help maintain both a vacuum level inside the vacuum interrupter and efficient working of the vacuum interrupter.

The metal vapor shield can also keep an electrostatic field uniformly distributed, both inside and outside of the vacuum interrupter, to ensure a longer life for the vacuum interrupter.

The metal vapor shield can protect a ceramic body of the vacuum interrupter from high levels of radiation during arcing and interruption, and prevent high level arcs from directly contacting the ceramic body.

Accordingly, measuring the gap between the metal vapor shield and the moving contact and the gap between the metal vapor shield and the fixed contact can ensure proper functioning of the vacuum interrupter. Additionally, the method can be used to measure the gap between the fixed contact portion and moving contact portion, also referred to as the primary gap.

The method can provide improved results when high-potential testing is performed on the vacuum interrupter. The method can allow a high-potential voltage to be applied across open contacts of the vacuum interrupter, allow the voltage to increase to a test value, and then measure leakage of current.

The method can allow for determination of very low quantities of current leakage for both AC high-potential tests and DC high-potential tests.

The high-potential tests can use the Penning Discharge Principle, The method can apply the Penning Discharge Principle because when a high voltage is applied to open contacts in a gas and a contact structure is surrounded with a magnetic field, an amount of current flow between plates is a function of gas pressure, applied voltage, and magnetic field.

The method can include creating a magnetic field using a field coil. The vacuum interrupter can be placed into the field coil, The magnetic field can be created using a flexible magnetic field coil, and then applying direct current (DC) to the flexible magnetic field coil. Next, a constant DC voltage, such as 10 kV, can be applied to open contacts, and current flow through the vacuum interrupter can be measured with the field coil. In one or more embodiments, the DC voltage can range from 10 volts to four thousand volts.

Since the magnetic field (D) and the applied voltage (DC) are both known, the only variable remaining is the pressure of the gas. If the relationship between the gas pressure and the current flow is known, then the internal pressure can be calculated based on the amount of current flow. The method can use this calculation.

One or more embodiments of the method do not generate X-rays during testing, in addition to providing accurate test values in the field using DC high-potential tests. In other methods, DC voltages, when applied across the gaps of the contacts, generate X-rays that are known to be harmful to operators without protection.

As such, the method allows vacuum interrupters to be tested in the field without the need for lead-based suits by reducing the potential of harm to operators. By not generating X-rays during testing, the method can save lives and prevent known harms to humans.

The method can be used to provide high-potential tests and contact-resistant tests to vacuum interrupters in the field to determine if the vacuum interrupters need to be replaced. The high-potential tests and contact-resistant tests can be quickly performed in the field using the method, such as in less than three hours.

The method can allow for testing of pressure inside the vacuum interrupters. Magnetrons and associated equipment have traditionally been used to test for pressure inside vacuum interrupters. Magnetrons and associated equipment are too bulky and heavy for efficient use in the field, are difficult to calibrate when moved, do not have trending and prediction tools for evaluating their tests, and require the removal of the vacuum interrupters from associated circuit breaker mechanisms.

The method can be easily implemented by less experienced operators in the field without requiring removal of the vacuum interrupters from associated circuit breakers.

The method can allow for testing, prediction, and trending of vacuum interrupter failure rates in the field.

One or more embodiments of the method can include applying a flexible magnetic field coil directly to the vacuum interrupter. The flexible magnetic field coil can be used on an entire pole, such as when the vacuum interrupter is not readily available.

Turning now to the figures, FIG. 1 depicts an embodiment of the electromagnetic testing device 59 having a connected body 10 and a closeable lid 11.

The electromagnetic testing device 59 can have a face plate 12. Capacitors beneath the face plate 12 can collect and release an electric charge. Also, rectifiers, relays, and a circuit board with the processor and the data storage can be disposed beneath the face plate 12.

The face plate 12 can have a power-in plug 14 for receiving 110 volts or 220 volts of AC current or another current from a power supply 93.

The capacitors beneath the face plate 12 can connect to additional plugs in the face plate 12, such as a high voltage output plug 15, a magnetic control positive output plug 16, and a magnetic control negative output plug 17.

The electromagnetic testing device 59 can connect to a flexible magnetic field coil 79 through a positive magnetic control wire 78 engaging the magnetic control positive output plug 16 and a negative magnetic control wire 77 engaging the magnetic control negative output plug 17.

In operation, upon actuation of the electromagnetic testing device 59, the electromagnetic testing device 59 can provide a current to the flexible magnetic field coil 79; thereby creating a magnetic field around an installed vacuum interrupter 80.

The installed vacuum interrupter 80 can be installed at an installed location 84, such as a power plant's circuit breaker switch room.

The installed vacuum interrupter 80 can be connected to the electromagnetic testing device 59 through a positive engagement wire 102 and a ground engagement wire 103.

The flexible magnetic field coil 79 can be wrapped around the installed vacuum interrupter 80.

The electromagnetic testing device 59 can have a ground plug 95 connecting to a ground wire 97 for grounding the electromagnetic testing device 59.

A test button 18 can be installed on the face plate 12 to actuate computer instructions in the data storage to actuate a test.

A display 85 on the face plate 12 can display calculated test results to a user.

The electromagnetic testing device 59 can be in communication with a client device 96 through network 94 for remote monitoring and actuation of the electromagnetic testing device 59.

In operation, when a strong magnetic field is applied around the vacuum interrupter 80, ions will move producing a current across an open contact. This ionization current is directly proportional to a pressure inside the vacuum interrupter 80. With a known ionic or current versus pressure curve, the pressure inside the vacuum interrupter 80 can be easily determined through the Penning Discharge Principle.

Figure 2:
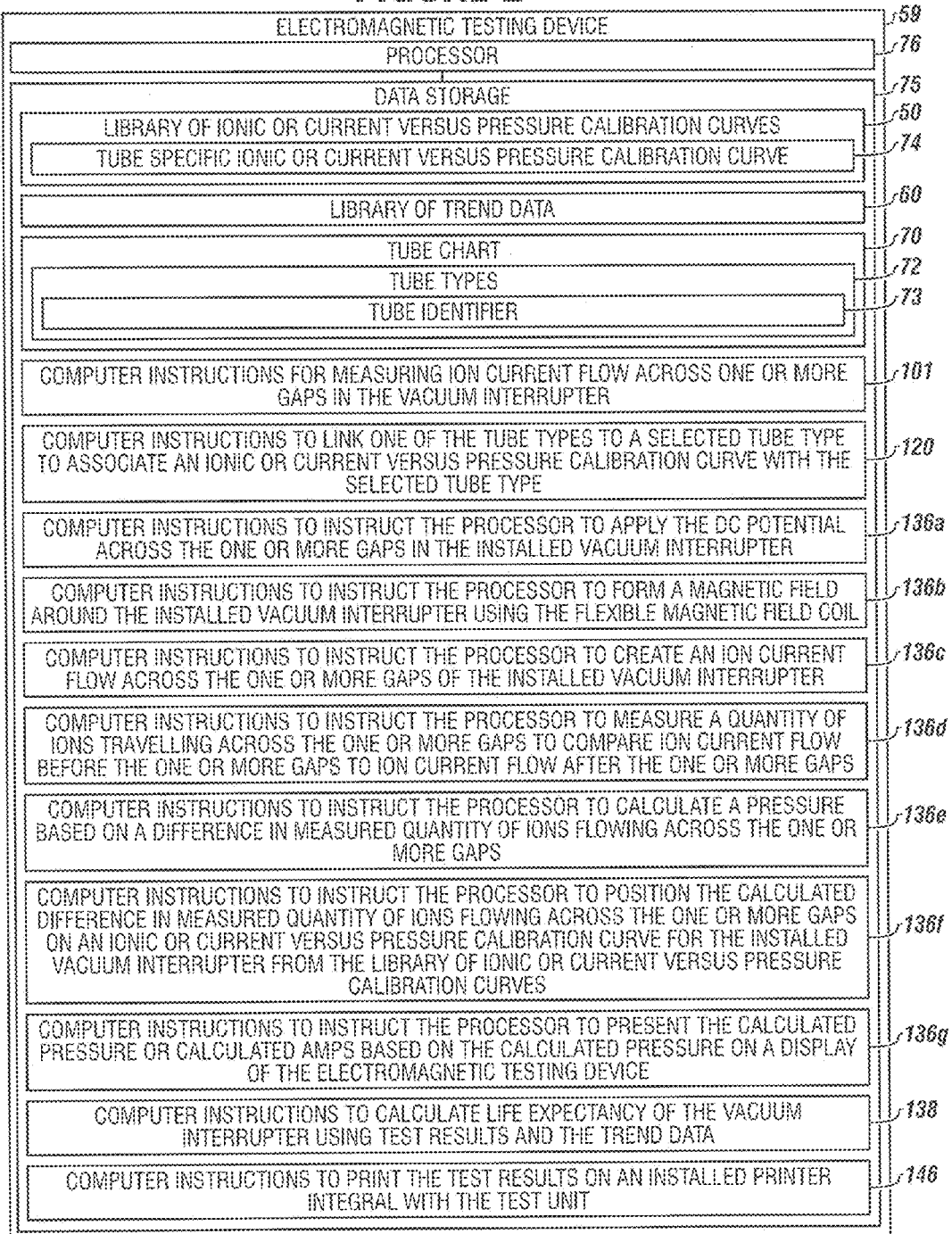
FIG. 2 depicts a data storage of the electromagnetic testing device in communication with a processor according to one or more embodiments.

FIG. 2 depicts the data storage 75 of the electromagnetic testing device 59 in communication with the processor 76.

A library of ionic or current versus pressure calibration curves 50 can be stored in the data storage 75.

A library of trend data 60 for each individual vacuum interrupter can be stored in the data storage 75.

The library of trend data 60 can include at least a vacuum interrupter serial number, a vacuum interrupter model or type, calculated pressure from other tests by the electromagnetic testing device testing identical model vacuum interrupters, calculated amp from other tests by the electromagnetic testing device testing identical model vacuum interrupter, or combinations thereof. Additional trend data can be stored in the library of trend data.

A tube chart 70 of tube types 72 can be stored in the data storage 75. Each tube type can have a tube identifier 73. Each tube identifier 73 can be linked to a tube specific ionic or current versus pressure calibration curve 74 in the library of ionic or current versus pressure calibration curves 50.

The data storage 75 can include computer instructions for measuring ion current flow across one or more gaps in the vacuum interrupter 101.

The data storage 75 can include computer instructions to link one of the tube types to a selected tube type to associate an ionic or current versus pressure calibration curve with the selected tube type 120.

The data storage 75 can include computer instructions to instruct the processor to apply the DC potential across the one or more gaps in the installed vacuum interrupter 136a.

The data storage 75 can include computer instructions to instruct the processor to form a magnetic field around the installed vacuum interrupter using the flexible magnetic field coil 136b.

The data storage 75 can include computer instructions to instruct the processor to create an ion current flow across the one or more gaps of the installed vacuum interrupter 136c.

The data storage 75 can include computer instructions to instruct the processor to measure a quantity of ions travelling across the one or more gaps to compare ion current flow before the one or more gaps to ion current flow after the one or more gaps 136d.

The data storage 75 can include computer instructions to instruct the processor to calculate a pressure based on a difference in measured quantity of ions flowing across the one or more gaps 136e.

The data storage 75 can include computer instructions to instruct the processor to position the calculated difference in measured quantity of ions flowing across the one or more gaps on an ionic or current versus pressure calibration curve for the installed vacuum interrupter from the library of ionic or current versus pressure calibration curves 136f.

The data storage 75 can include computer instructions to instruct the processor to present the calculated pressure or calculated amps based on the calculated pressure on a display of the electromagnetic testing device 136g.

The data storage 75 can include computer instructions to calculate life expectancy of the vacuum interrupter using test results and the trend data 138.

The data storage 75 can include computer instructions to print the test results on an installed printer integrated with the test unit 146.

Figure 3:
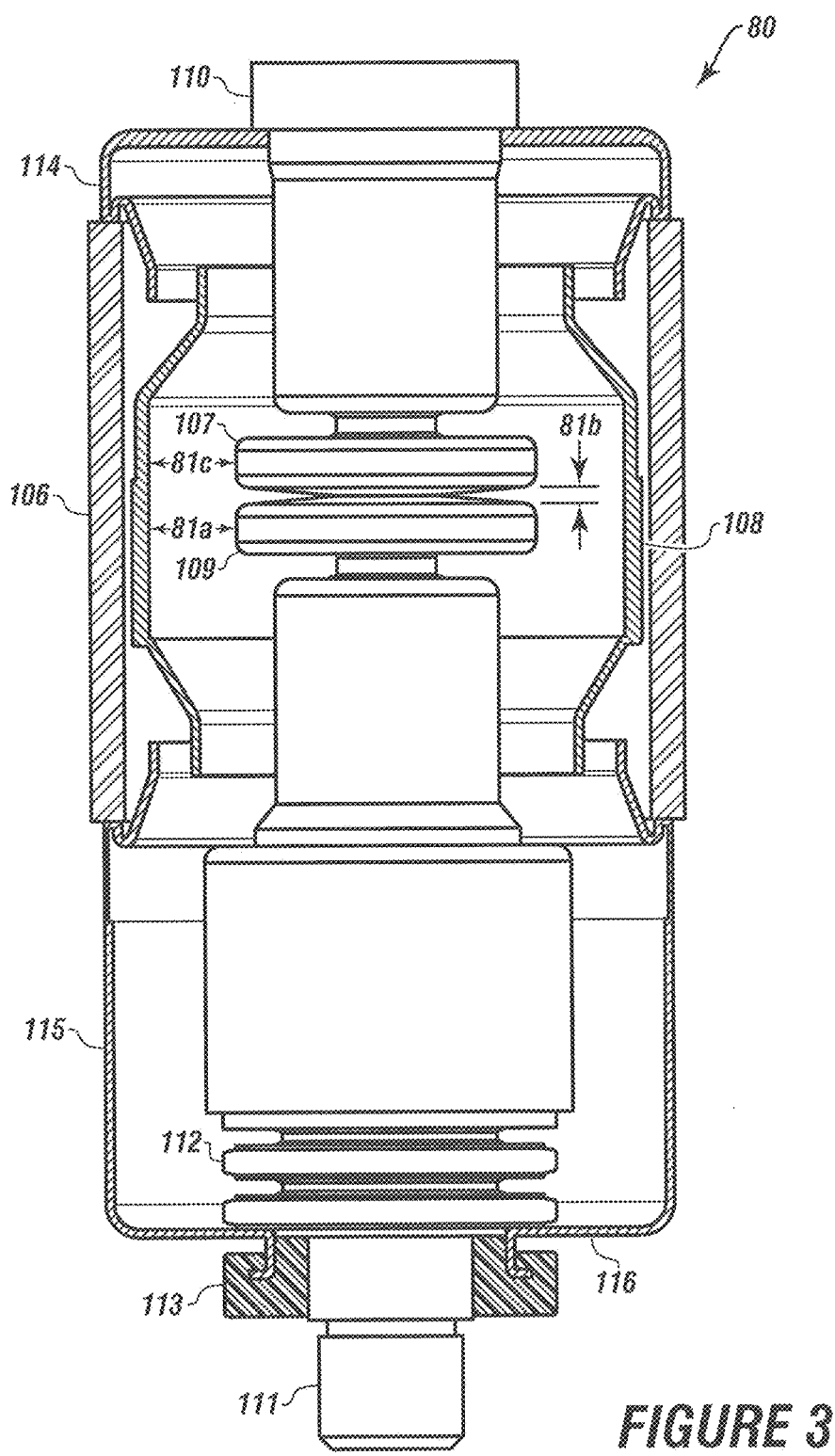
FIG. 3 depicts a vacuum interrupter according to one or more embodiments.

FIG. 3 depicts an embodiment of a vacuum interrupter 80 with a body 106, also referred to as an insulator body. The body 106 can be made of glass, metal, ceramic, or combinations of these materials, forming a case.

The body 106 can have one or two segments.

The vacuum interrupter 80 can have a top 114, bottom 115, and mounting means 116.

The vacuum interrupter 80 can have a fixed contact 107, which can be metal, slotted, solid, or combinations thereof. The fixed contact 107 can engage a fixed contact stem 110.

One or more embodiments of the vacuum interrupter 80 can have a vapor shield 108, which can be for shielding metal vapor or other contaminates. The vapor shield 108 can collect metal that comes off of contacts during application of current to the contact, can stop sputtering material from contaminating the inside of the case that occurs, and can control flashing.

The vacuum interrupter 80 can have a moving contact 109 connected to a moving contact stem 111 surrounded by a moving contact guide 113, which can be made of plastic.

A bellows 112, which can be made of stainless steel, can be disposed within the bottom 115 between the moving contact 109 and moving contact stem 111.

In operation, the moving contact stem 111 can engage a circuit breaker motor, which is not shown.

A first gap 81a can be formed between the moving contact 109 and the vapor shield 108, a second gap 81b can be formed between the fixed contact 107 and the moving contact 109, and a third gap 81c can be formed between the fixed contact 107 and the vapor shield 108.

FIG. 4 depicts another embodiment of the electromagnetic testing device 59 having a housing 19.

The face plate 12 can be disposed on the housing 19, and a circuit board that contains the data storage with the processor can be disposed beneath the face plate 12. The circuit board can connect to at least one capacitor beneath the face plate 12 for accepting power from a power in plug engaging the power supply that can be connected to the back of the housing 19.

The power supply can provide power to the processor of the electromagnetic testing device 59.

An on/off switch 9 can be used to turn the electromagnetic testing device 59 on and off.

Prior to initiating testing, a user can select a tube type, which can be displayed on a tube type display 20, such as by using a selector button 21 that connects to the tube chart in the data storage, a number up selector 22, and a number down selector 23.

The user can also select between a single gap vacuum interrupter test and a double gap vacuum interrupter test, such as by reconnecting test leads to shield contacts or across contacts.

Additionally, the user can select, using a test selector switch 25, from a fixed magnetic field test using non-flexible canisters of magnetic coils having a fixed inner diameter and a test using the flexible magnetic field coil.

To initiate the testing by the electromagnetic testing device 59, a test button 18 can be depressed to actuate a series of computer instructions in the data storage for powering a capacitor, discharging the capacitor into the vacuum interrupter while powering the magnetic field, and receiving signals from the magnetic field from a signal input wire that engages a signal input plug 26.

Computations performed using the computer instructions can be displayed on displays in the face plate 12. For example, results can be presented on a main pressure or amp results display 27 and an exponential factor display 28. Also, a unit choice can be indicated as Pascals or as Amps using light emitting diodes "LED" lights 29a and 29b.

A print button 30 can be used to actuate computer instructions in the data storage to print test results on a built in printer 31.

In one or more embodiments, the electromagnetic testing device 59 can be lightweight and usable for labs and shops. For example, the electromagnetic testing device 59 can weigh less than ten pounds. Additionally, the electromagnetic testing device 59 can have a measurement range from about $1 \times 10^{-5}$ Pascals to about $1 \times 10^{-1}$ Pascals. The measurement accuracy can be less than 10 percent for measurements from $1 \times 10^{-4}$ Pascals and $1 \times 10^{-1}$.

In operation, the electromagnetic testing device 59 can be easy and safe to operate without causing damage to the vacuum interrupter during testing, and without jeopardizing the life of the user during testing.

The electromagnetic testing device 59 can also have a coil choice selector 24 for selecting a flexible magnetic field coil.

FIGS. 5A and 5B depict details of two different types of fixed inner diameter magnetic coils 51a and 51b that can be used to test vacuum interrupters instead of using a flexible magnetic field coil.

Each fixed inner diameter magnetic coil 51a and 51b can have an insulated metal housing 33a and 33b that has a central chamber 37a and 37b for receiving vacuum interrupters 80a and 80b.

A plurality of insulated copper wires 38a and 38b can be disposed around the central chambers 37a and 37b in the insulated metal housings 33a and 33b to create the magnetic field.

A copper plate can be on a bottom of the inside of the insulated metal housings 33a and 33b for connecting to the vacuum interrupters 80a and 80b that have been removed from a breaker or contactor. As such, a consistent and uniform magnetic field can be formed for accurate vacuum interrupter condition measurements. The fixed inner diameter magnetic coils 51a and 51b can have various inner diameter sizes.

Each fixed inner diameter magnetic coil 51a and 51b can have positive magnetic connections 34a and 34b and negative magnetic connections 35a and 35b.

Each fixed inner diameter magnetic coil 51a and 51b can have a fixed inner diameter 32a and 32b.

FIGS. 6A and 6B depict an embodiment of the method.

The method can include creating and installing the library of ionic or current versus pressure calibration curves for individual vacuum interrupters in the data storage of the electromagnetic testing device, as illustrated by box 6000.

The method can include creating and installing the library of trend data for each individual vacuum interrupter in the data storage of the electromagnetic testing device, as illustrated by box 6002.

The method can include creating and installing the tube chart in the data storage of the electromagnetic testing device, as illustrated by box 6004.

The method can include placing an installed vacuum interrupter within a flexible magnetic field coil without removing the installed vacuum interrupter from an installed location in an operating unit, as illustrated by box 6006.

The method can include using a closed circuit test and actuating a DC potential from the electromagnetic testing device to cross the first gap in the installed vacuum interrupter between a vapor shield in the installed vacuum interrupter and a contact assembly in the installed vacuum interrupter, as illustrated by box 6008a; or the method can include using an open circuit test and placing the DC potential across the first gap and a second gap a first contact and a second contact of the installed vacuum interrupter in the open position allowing ion current flow across the first gap and second gap, as illustrated by box 6008b.

The method can include selecting a tube type using a pressure sensitive display on the electromagnetic testing device, as illustrated by box 6010.

The method can include displaying the selected tube type for the installed vacuum interrupter on a display of the electromagnetic testing device, as illustrated by box 6012.

The method can include measuring ion current flow across the first gap and/or the second gap of the installed vacuum interrupter by using a signal from the flexible magnetic field coil and using computer instructions in the data storage for measuring ion current flow, as illustrated by box 6014.

The method can include linking one of the tube types to the selected tube type to associate an ionic or current versus pressure calibration curve with the selected tube type, as illustrated by box 6016.

The method can include selecting an output reading for the electromagnetic testing device consisting of either a direct pressure reading in Pascals or an ionic current reading in amps, as illustrated by box 6018.

The method can include actuating testing by the electromagnetic testing device by using computer instructions in the data storage to instruct the processor to: apply the DC potential across the first gap and/or the second gap in the installed vacuum interrupter, form the magnetic field around the installed vacuum interrupter using the flexible magnetic field coil, create the ion current flow across the first gap and/or the second gap of the installed vacuum interrupter, measure the quantity of ions travelling across the first gap and/or the second gap to compare ion current flow before the first gap and/or the second gap to ion current flow after the first gap and/or second gap, and calculate a pressure based on the difference in measured quantity of ions flowing across the first gap and/or the second gap, as illustrated by box 6020.

The method can include using a closed circuit test and actuating a DC potential from the electromagnetic testing device to cross the third gap in the installed vacuum interrupter between the vapor shield in the installed vacuum interrupter and the contact assembly in the installed vacuum interrupter, as illustrated by box 6022.

The method can include measuring ion current flow across the third gap of the installed vacuum interrupter by using a signal from the flexible magnetic field coil and using computer instructions in the data, storage for measuring ion current flow, as illustrated by box 6024.

The method can include actuating testing by the electromagnetic testing device by using computer instructions in the data storage to instruct the processor to: apply the DC potential across the third gap in the installed vacuum interrupter, form the magnetic field around the installed vacuum interrupter using the flexible magnetic field coil, create the ion current flow across the first gap and/or the second gap of the installed vacuum interrupter, measure the quantity of ions travelling across the third gap to compare ion current flow before the third gap to ion current flow after the third gap, and calculate a pressure based on the difference in measured quantity of ions flowing across the third gap, as illustrated by box 6026.

The method can include determining an anticipated life expectancy of the installed vacuum interrupter by: positioning the calculated amp or calculated pressure on the ionic or current versus pressure calibration curve for the installed vacuum interrupter and identifying the trend data from the library of trend data corresponding to the installed vacuum interrupter and to the calculated pressure or to the calculated amp of the installed vacuum interrupter to determine the anticipated life expectancy in years and months for the installed vacuum interrupter, as illustrated by box 6028.

The method can include providing the calculated amp or calculated pressure to an RS232 interface or a printer, as illustrated by box 6030.

The method can include using a printer that is integrated with the electromagnetic testing device to print the calculated amp or calculated pressure and to provide a location of the calculated amp or calculated pressure on the ionic or current versus pressure calibration curve of the installed vacuum interrupter, as illustrated by box 6032.

The method can include resetting the display using a reset button on the electromagnetic testing device to: turn off an LED light, clear the calculated amp, clear the calculated pressure, or combinations thereof, as illustrated by box 6034.

The method can include using the LED light to indicate when the electromagnetic testing device is performing the test, as illustrated by box 6036.

The method can include connecting the processor with a network for communication to a client device remote to the processor, as illustrated by box 6038.

While these embodiments have been described with emphasis on the embodiments, it should be understood that within the scope of the appended claims, the embodiments might be practiced other than as specifically described herein.

Figure 7:
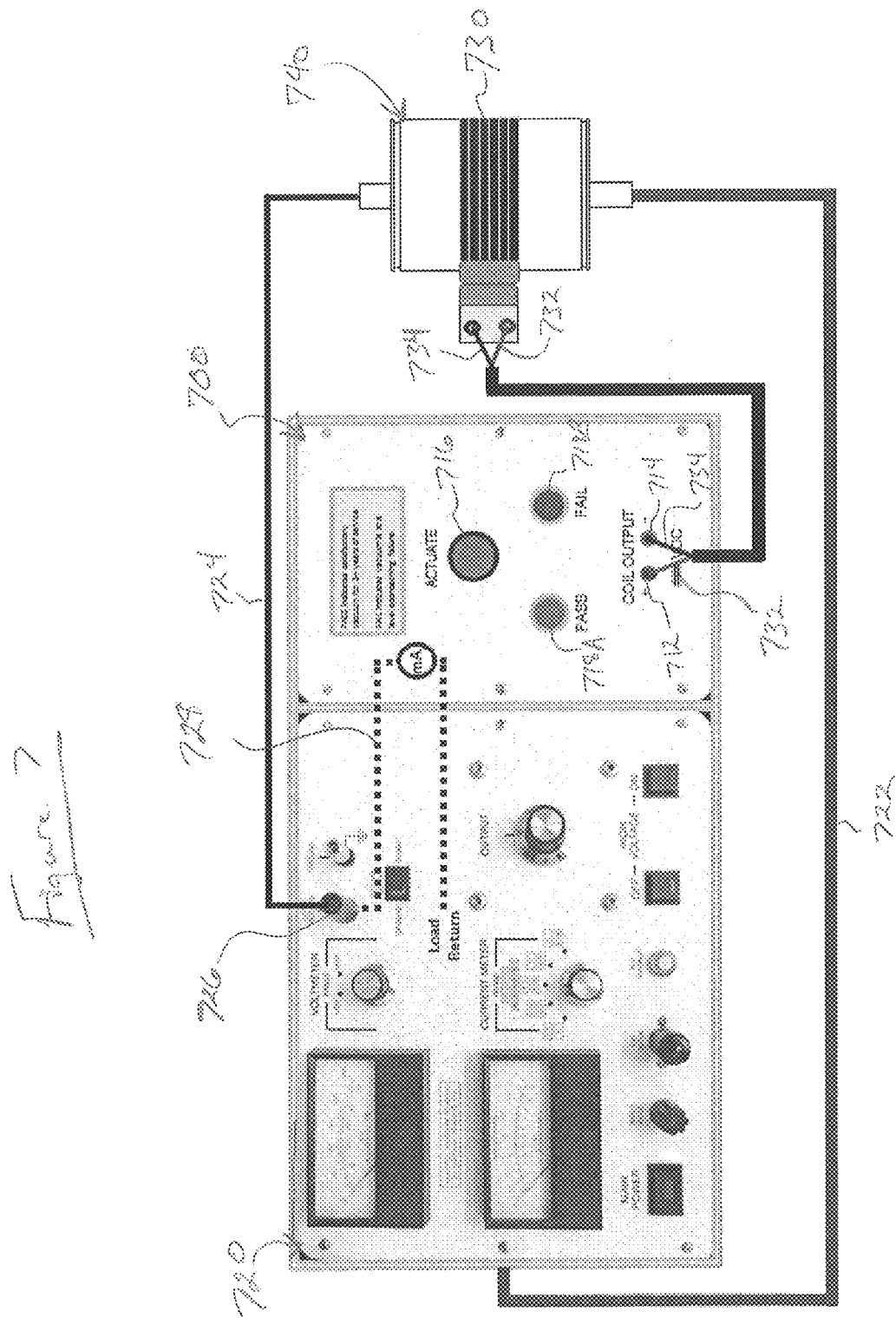
FIG. 7 illustrates an example of an integrated embodiment of the electromagnetic testing device.

For example, FIG. 7 illustrates an example embodiment of an electromagnetic testing device 700 similar to that described above and illustrated in FIGS. 1 and 4, wherein the electromagnetic testing device 700 is shown integrated with a high-potential testing portion 720. The high-potential testing portion 720 may, in some embodiments, comprise standalone circuitry referred to as a hipot tester. In other embodiments, such as that shown in FIG. 7, the hipot tester circuitry (i.e., high-potential testing portion 720) may be integrated with the electromagnetic testing device 700. The electromagnetic testing device 700, including high-potential testing portion 720, operates in accordance with the foregoing disclosure.

The electromagnetic testing device 700 is connected to an electromagnetic field coil 730 through a positive magnetic control wire 732 engaging magnetic control positive output plug 712 and a negative magnetic control wire 734 engaging magnetic control negative output plug 714. The electromagnetic field coil 730 is wrapped around an installed vacuum interrupter 740. During testing, the electromagnetic testing device 700 provides a current to the electromagnetic field coil 730 to create a magnetic field around the installed vacuum interrupter 740.

The high-potential testing portion 720 of the electromagnetic testing device 700 is connected to the vacuum interrupter 740 via a supply wire 722 and a return wire 724. During testing, the high-potential testing portion 720 applies a DC potential across the open contacts the vacuum interrupter 740 by applying a supply voltage via the supply wire 722 and receiving a load return from the return wire 724, wherein the return load is received at a load return port 726.

In the embodiment illustrated in FIG. 7, the electromagnetic testing device 700 is integrated with the high-potential testing portion 720, and includes an integrated current sensing circuit 728 in series with the load return 726. As discussed in greater detail below, the integrated current sensing circuit 728 is used to control Pass/Fail lights 718 or other suitable status indicators to indicate the condition of the vacuum interrupter 740. Electromagnetic testing device 700 provides the benefit of being able to detect poor vacuum in installed vacuum interrupters prior to failure. In some embodiments, the electromagnetic testing device 700 is capable of performing two tests simultaneously.

Testing of the vacuum interrupter 740 is conducted via the electromagnetic testing device 700 in accordance with the foregoing disclosure. Thus, the high-potential testing portion 720 applies a DC potential across the open contacts of the vacuum interrupter 740. When the high DC voltage is applied across the open contacts of the vacuum interrupter 740, gas molecules inside the vacuum interrupter 740 are ionized. By applying a strong magnetic field via the magnetic field coil 730, current will flow between the contacts of the vacuum interrupter 740 due to the entrapment of the ions in the magnetic field. This ion current is proportional to the gas pressure inside the vacuum interrupter 740, and may be used to determine the predicted usable life of the vacuum interrupter 740.

The electromagnetic testing device 700 includes an actuate button 716 (or other suitable type of switch) which, when pressed, activates the magnetic field to initiate testing of the vacuum interrupter 740. Upon completion of the testing, indication of the condition of the vacuum interrupter 740 is provided by a condition indicator such as, for example, Pass/Fail lights 718. For example, a vacuum interrupter 740 having a relatively good vacuum will generate a low ion current (e.g., less than 1 mA) during testing, wherein the low ion current is such that it will not be great enough to activate current sensing circuitry in the high-potential testing portion 720 (or is otherwise below a low current threshold). When low ion current is detected (or not detected), the green "Pass" light 718A is illuminated. Conversely, a vacuum interrupter 740 with a relatively poor vacuum will generate a high ion current (e.g., greater than 1 mA) during testing, wherein the high ion current is such that it will be great enough to activate current sensing circuitry in the high-potential testing portion 720 (or is otherwise above a low current threshold). When high ion current is detected, the red "Fail" light 718B is illuminated.

In some embodiments, illumination of the "Pass" light 718A is indicative of an acceptable predicted usable life of the vacuum interrupter 740. For example, illumination of the green "Pass" light 718A may be indicative of five or more years of a usable life of the vacuum interrupter 740. Illumination of the "Fail" light 718B may be indicative of an unacceptable predicted usable life of the vacuum interrupter 740. For example, illumination of the red "Fail" light 718B made be indicative of less than five years of a usable life of the vacuum interrupter 740.

Other implementations and embodiments may include further modifications to the electromagnetic testing device 700. For example, some embodiments may feature three (or more) condition indicator lights such as, for example, red, yellow, and green lights. In such embodiments, the green light may be indicative of an acceptable predicted usable life (e.g., more than five years), the yellow light may be indicative of a less acceptable predicted usable life (e.g., between three and five years), and the red light may be indicative of a failed vacuum interrupter or a vacuum interrupter having an unacceptable predicted usable life (e.g., less than three years). Such an embodiment may be accomplished by applying various currents to the magnetic field coil 730 in increasing order, and determining, for each current level, whether a high ion current is detected before moving to the next current level. For example, a first current may be applied such that the magnetic field coil 730 produces a first magnetic field (e.g., about 200 Gauss), and a determination is made whether the ion current is "high" or "low." If the ion current is high, then the red light is illuminated. Otherwise, the current is increased until a second magnetic field is reached (e.g., about 300 Gauss), and a determination is made whether the ion current is high or low. If the ion current is high, then the yellow light is illuminated. Otherwise, the green light is illuminated. It should be understood that the operations of controlling the current/magnetic field, the associated timing, and other operations discussed herein are capable of being controlled using a programmable logic controller or other combinations of hardware and software.

It should be appreciated that the acceptable and unacceptable predicted usable life examples used herein are merely examples. Thus, other predictions of a vacuum interrupter usable life may be used for the various acceptable/unacceptable conditions. For example, an acceptable predicted usable life may be ten or more years. Additionally, the current and Gauss measurements provided herein are merely exemplary. Similarly, the examples of a "high" or "low" ion current used herein are not intended to be limiting. Thus, other ion currents may be determined to be a "high" or "low" ion current. For example, a low ion current may be determined to be any value between 1 mA and 10 mA (or any other determined value). Thus, various combinations of low and high ion current values may be used to represent various acceptable predicted usable life values depending upon various testing parameters and/or user settings. For example, in some embodiments, a low ion current may be 3 mA, which may correlate to an acceptable predicted usable life of five years.

Figure 8B:
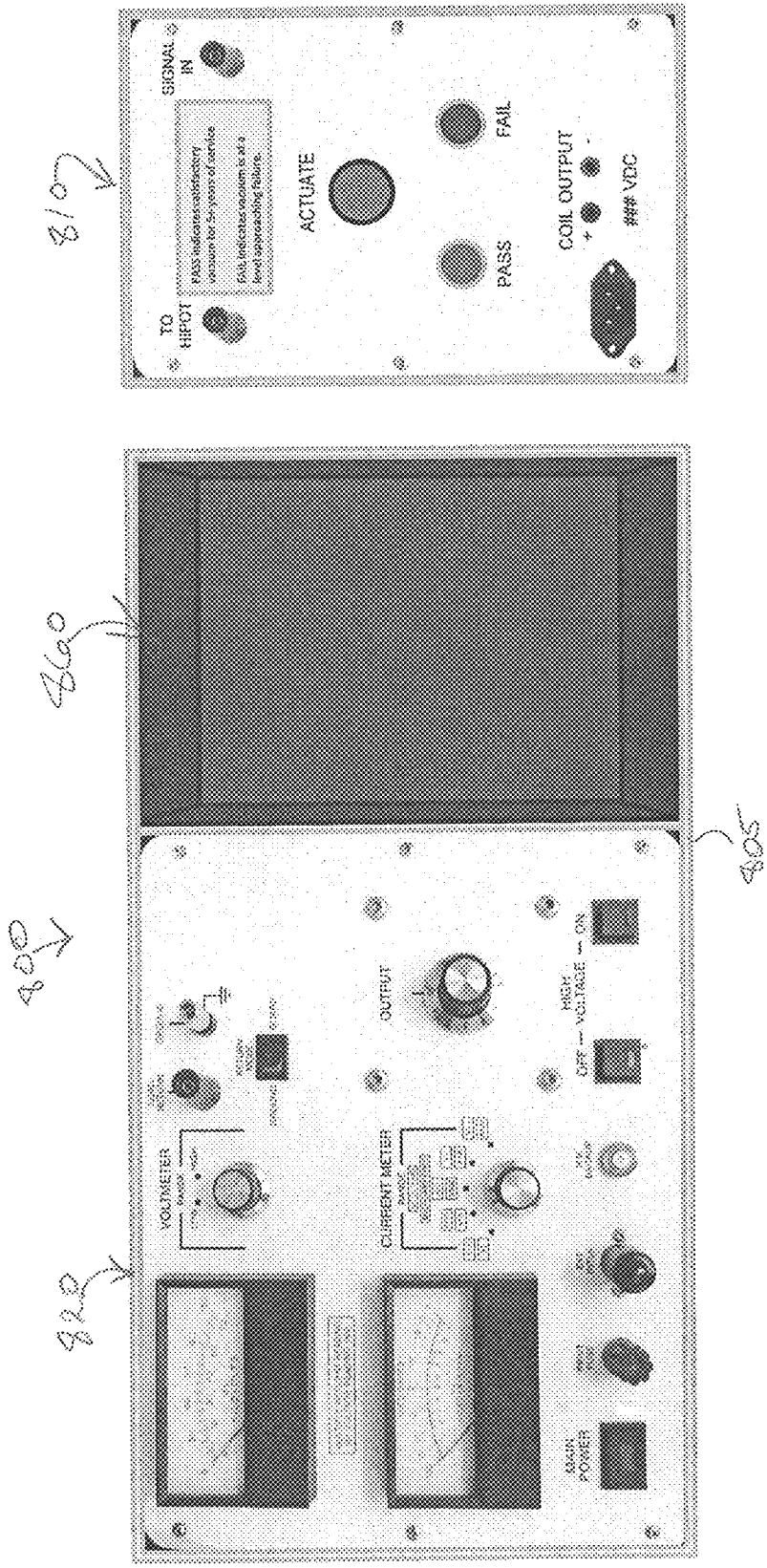

Reference is now made to FIGS. 8A and 8B, which illustrate another example embodiment of the disclosed electromagnetic testing device 800. The electromagnetic testing device 800 is similar to that shown in FIG. 7, except that the electromagnetic testing device 800 is a partially integrated embodiment featuring a housing 805 for both a Magnetron Atmospheric Condition (MAC) unit 810 and a high-potential testing unit (hipot unit) 820. The MAC unit 810 features a power outlet 812, signal in port 814, and a high-potential testing output port 816. The signal in port 814 receives the return wire 724 that is connected to the vacuum interrupter 740, and the high-potential testing output port 816 provides a connection 818 to the load return port 822 of the high-potential testing portion 820. The MAC unit 810 also features a magnetic control positive output plug 712 and a magnetic control negative output plug 714 for connecting the MAC unit 810 to the flexible electromagnetic field coil 730 via the positive magnetic control wire 732 and the negative magnetic control wire 734. The MAC unit 810 also includes the actuate button 716 and condition indicator lights 718.

The partially integrated embodiment of the electromagnetic testing device 800 allows a user to connect the MAC unit 810 to an existing high-potential testing unit 820 without modification to the MAC unit 810 or high-potential testing unit 820. The current sensing circuitry (not shown) of the MAC unit 810 connects in series with the load return port 822 of the high-potential testing unit 820 via connection 818. Thus, the MAC unit 810 is removable, as shown in FIG. 8B. Once the MAC unit 810 is removed, the housing 805 provides a compartment 860, which doubles as cable storage or other use. Should be understood that the MAC unit 810's capable of being used with any high-potential testing unit 820, including any DC hipot.

Figure 9:
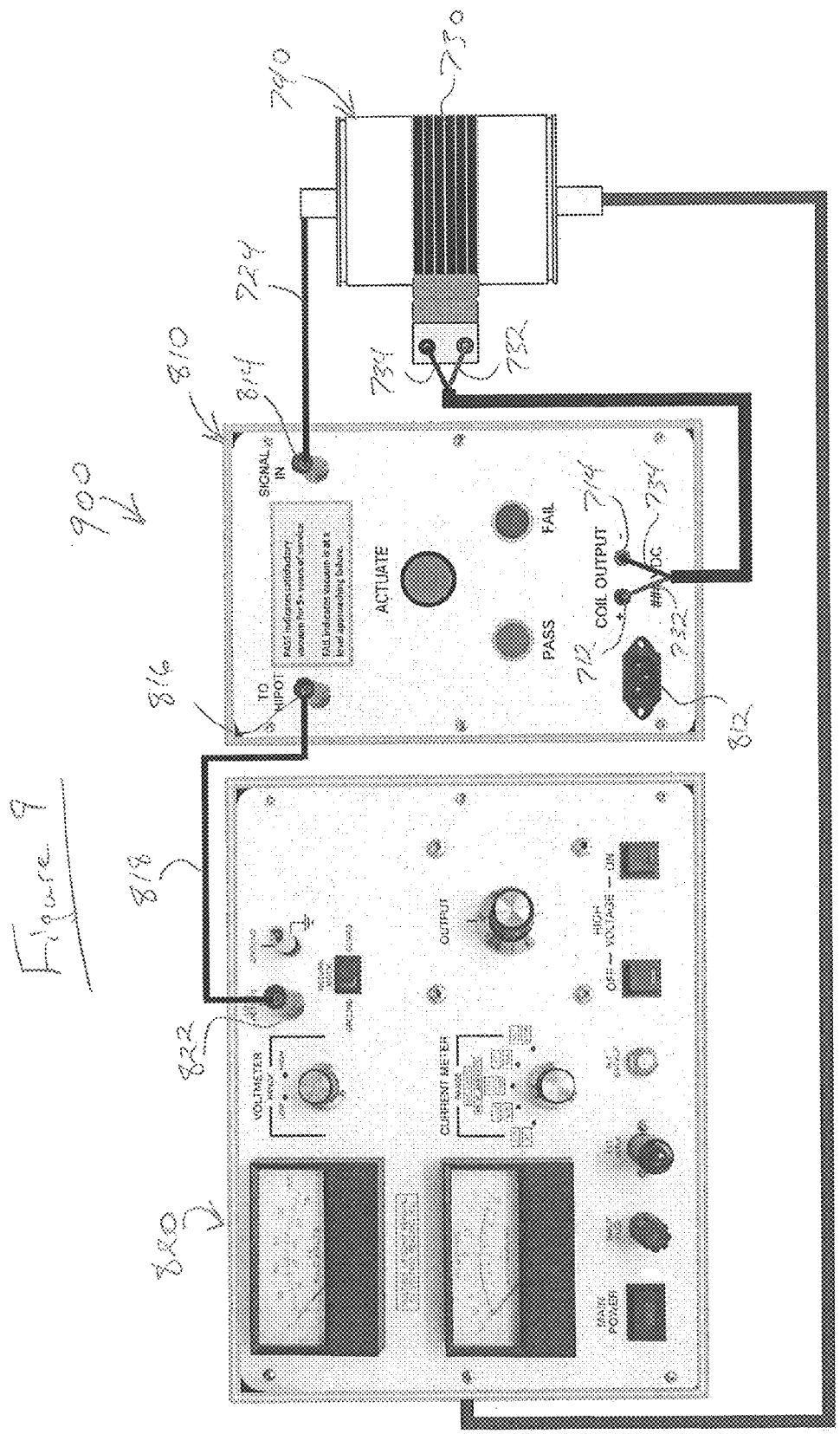
FIG. 9 illustrates an example of a modular embodiment of the electromagnetic testing device.

Reference is now made FIG. 9, which illustrates another example embodiment of the disclosed electromagnetic testing device 900. The electromagnetic testing device 900 is similar to that shown in FIG. 8, except that the electromagnetic testing device 900 is a modular embodiment where the MAC unit 810 is separate from the high-potential testing unit 820. Thus, the MAC unit 810 is a stand-alone unit for use with a standard hipot unit (i.e., high-potential testing unit 820). As shown in FIG. 9, the MAC unit 810 is connected in line with the high-potential testing unit 820 load return terminal 822 via the connection 818. In accordance with the foregoing disclosure, the MAC unit 810 has inline current sensing circuitry (not shown) that activates the condition indicator lights 718 according to preset current limits.

Figure 10:
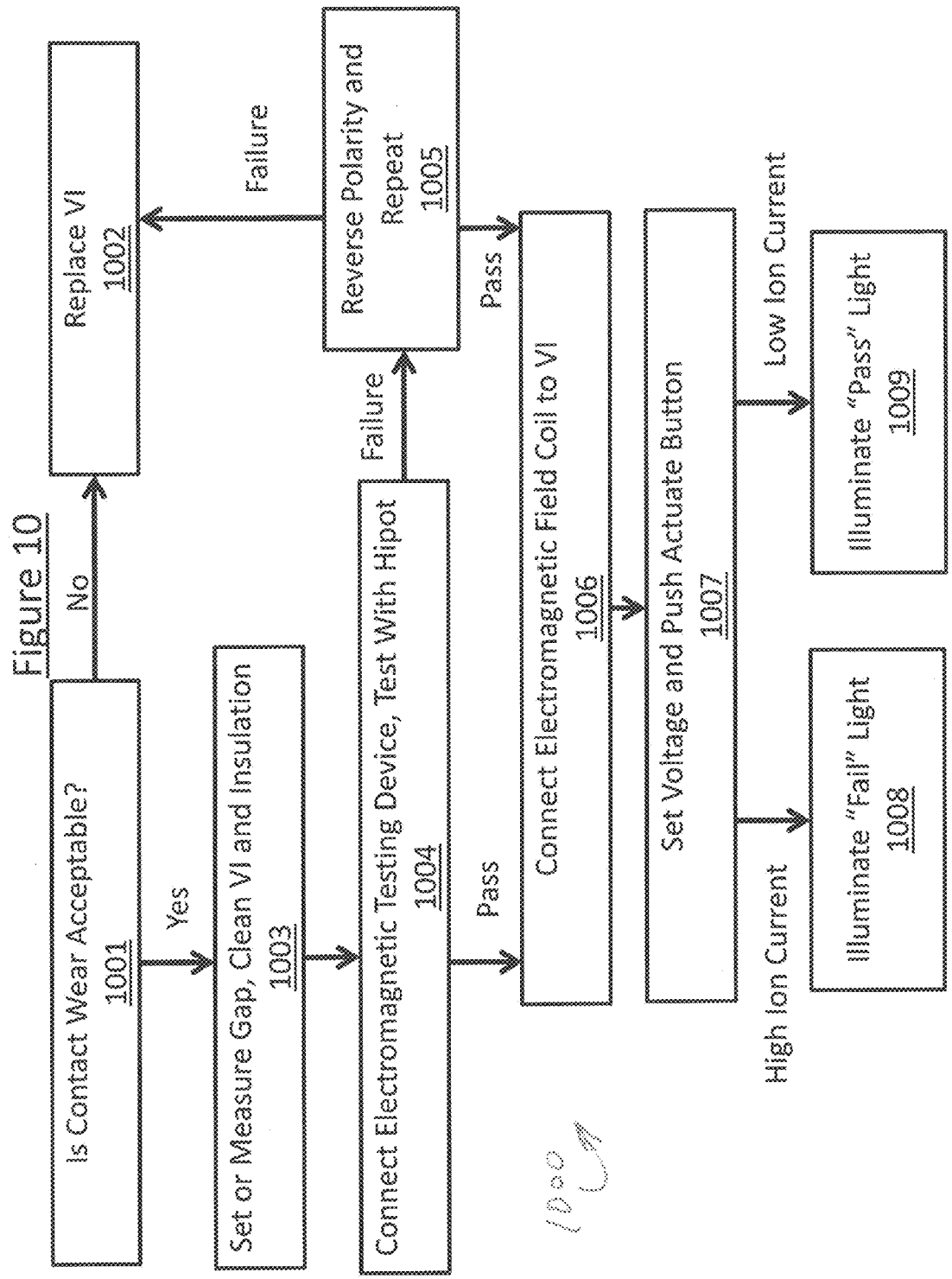
FIG. 10 illustrates an example of a testing procedure for use in accordance with the electromagnetic testing device illustrated in FIG. 7.

FIG. 10 illustrates an example of a testing procedure in accordance with the foregoing disclosure. The flowchart 1000 in FIG. 10 is discussed with reference to the electromagnetic testing device 700 illustrated in FIG. 7, but also includes testing procedure that is discussed with respect to other portions of the foregoing disclosure. At 1001, a user inspects contact wear for the installed vacuum interrupter 740. If contact wear is outside the parameters of accepted tolerances, then the vacuum interrupter 740 is replaced at 1002. If contact wear is within the parameters of accepted tolerances, the user sets or measures the gap, and cleans the vacuum interrupter 740 and insulation at 1003. At 1004, the electromagnetic testing device 700 is connected and testing is performed using the high-potential testing portion (hipot) 720. If the testing yields a failure of the vacuum interrupter 740, then the polarity of the hipot connection is reversed at 1005. If the testing yields a second failure, then the vacuum interrupter 740 is replaced. If the testing yields a pass on the first try or upon reversing the polarity, then the electromagnetic field coil 730 is applied to the vacuum interrupter 740 at 1006. At 1007, the voltage is set on the high-potential testing portion 720, and the actuate button 716 is pushed on the electromagnetic testing device 700 to initiate testing. If the electromagnetic testing device 700 detects a high ion current, the red "Fail" light 718B is illuminated at 1008, thereby indicating that the vacuum interrupter 740 has an unacceptable predicted usable life (e.g., less than five years). If the electromagnetic testing device 700 detects a low ion current, the green "Pass" light 718A is illuminated at 1009, thereby indicating that the vacuum interrupter 740 has an acceptable predicted usable life (e.g., greater than five years).

What is claimed is:

1. A method for predicting a usable life of a vacuum interrupter, the method comprising:
    placing a magnetic field generator adjacent to an installed vacuum interrupter;
    generating a magnetic field around the installed vacuum interrupter using the magnetic field generator;
    measuring ion current flow across one or more open contacts of the installed vacuum interrupter;
    comparing the measured ion current flow to a threshold value; and
    indicating a first condition of the vacuum interrupter.

2. The method of claim 1, wherein the threshold value corresponds to an acceptable predicted usable life of the installed vacuum interrupter.

3. The method of claim 1, wherein the first condition of the vacuum interrupter is an acceptable condition if the measured ion current flow is less than the threshold value.

4. The method of claim 1, wherein the first condition of the vacuum interrupter is an unacceptable condition if the measured ion current flow is greater than the threshold value.

5. The method of claim 1, wherein the indication of the first condition comprises illuminating a first light if the first condition is an acceptable condition and illuminating a second light if the first condition is an unacceptable condition.

6. A method for predicting a usable life of a vacuum interrupter, the method comprising:
    placing a magnetic field generator adjacent to an installed vacuum interrupter;
    generating a magnetic field around the installed vacuum interrupter using the magnetic field generator;
    measuring a first ion current flow across one or more open contacts of the installed vacuum interrupter;
    comparing the first measured ion current flow to a threshold value;
    if the first measured ion current flow is greater than the threshold value, indicating a first condition of the vacuum interrupter; and
    if the first measured ion current flow is less than the threshold value:
        increasing the magnetic field around the installed vacuum interrupter;
        measuring a second ion current flow across the one or more open contacts;
        comparing the second measured ion current flow to the threshold value; and
        indicating a second condition of the vacuum interrupter.

7. The method of claim 6, wherein the indication of the first condition comprises illuminating a first light if the first condition is an unacceptable condition.

8. The method of claim 6, wherein the indication of the second condition comprises illuminating a second light if the second condition is an acceptable condition, or illuminating a third light if the second condition is a less acceptable condition.

9. The method of claim 6, wherein the threshold value corresponds to an acceptable predicted usable life of the vacuum interrupter.

10. The method of claim 6, wherein the first condition of the vacuum interrupter is an unacceptable condition if the measured first ion current flow is greater than the threshold value.

11. The method of claim 6, wherein the second condition of the vacuum interrupter is a less acceptable condition if the measured second ion current flow is greater than the threshold value, and is an acceptable condition if the measured second ion current flow is less than the threshold value.

12. A system for predicting a usable life of a vacuum interrupter, the system comprising:
a magnetic field generator configured to be placed adjacent to an installed vacuum interrupter;
wherein the magnetic field generator is configured to generate a magnetic field around the installed vacuum interrupter;
current sensing circuitry configured to measure ion current flow across one or more open contacts of the installed vacuum interrupter and to compare the measured ion current flow to a threshold value; and
a condition indicator configured to indicate a first condition of the vacuum interrupter.

13. The system of claim 12, wherein the condition indicator comprises one or more lights to indicate a condition of the installed vacuum interrupter.

14. The system of claim 13, wherein the condition comprises one of an acceptable, a less acceptable, and an unacceptable condition.

15. The system of claim 12, wherein the threshold value corresponds to an acceptable predicted usable life of the vacuum interrupter.

16. The system of claim 12, wherein the first condition of the vacuum interrupter is an acceptable condition if the measured ion current flow is less than the threshold value.

17. The system of claim 12, wherein the first condition of the vacuum interrupter is an unacceptable condition if the measured ion current flow is greater than the threshold value.

18. The method of claim 1, wherein the magnetic field generator comprises a flexible magnetic field coil.

19. The method of claim 18, further comprising causing a DC potential to be applied across the one or more open contacts of the installed vacuum interrupter.

20. The method of claim 6, wherein the magnetic field generator comprises a flexible magnetic field coil.

21. The method of claim 20, further comprising causing a DC potential to be applied across the one or more open contacts of the installed vacuum interrupter.

22. The system of claim 12, wherein the magnetic field generator comprises a flexible magnetic field coil configured to be placed around the installed vacuum interrupter; and further comprising a current generator configured to generate a magnetic field around the installed vacuum interrupter using the flexible magnetic field coil.

23. The system of claim 22, further comprising control circuitry configured to cause a DC potential to be applied across the one or more open contacts of the installed vacuum interrupter.

24. The system of claim 23, further comprising a high-potential testing unit configured to apply the DC potential across the one or more open contacts of the installed vacuum interrupter.

* * * * *